Figure 1:
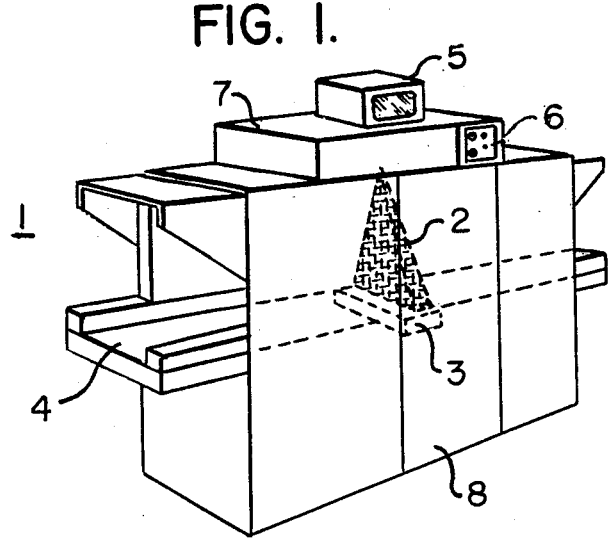

United States Patent [19]

Paolini

[11] Patent Number: 4,644,578
[45] Date of Patent: Feb. 17, 1987

[54] DETECTION ARRANGEMENTS FOR X-RAY SECURITY SYSTEMS

[75] Inventor: Francis R. Paolini, Stamford, Conn.

[73] Assignee: North American Philips Corporation, New York, N.Y.

[21] Appl. No.: 453,421

[22] Filed: Dec. 27, 1982

[51] Int. Cl.[4] .............................................. G03B 41/16
[52] U.S. Cl. ...................................... 378/146; 378/57
[58] Field of Search .................................. 378/146, 57

[56] References Cited

U.S. PATENT DOCUMENTS

| 3,944,833 | 3/1976 | Hounsfield | 378/19 |
| 4,179,100 | 12/1979 | Sashin | 378/146 |
| 4,433,427 | 2/1984 | Barnea | 378/146 |

Primary Examiner—Craig E. Church
Attorney, Agent, or Firm—Paul R. Miller

[57] ABSTRACT

The present invention provides an improvement to a digital system for reading out image information of items passing on a conveyor belt through an X-ray fan-beam. The improvement involves an oscillating screen or mask moving between the items and detector elements with the mask having openings in registration with at most one half of each of several detector elements. The mask oscillates over the detector elements to expose alternate portions of the radiation detecting surface of each of the detector elements to the incident X-rays.

8 Claims, 5 Drawing Figures

DETECTION ARRANGEMENTS FOR X-RAY SECURITY SYSTEMS

The present invention is directed to an arrangement for improving the spatial resolution of linear arrays of discrete detectors in baggage security systems. Present structures of X-ray security systems utilize digital techniques to form and process images of objects being inspected, and the invention provides the use of an oscillating mask to substantially improve the resolving power of such arrangements.

In typical X-ray baggage inspection systems of the past, fan-beam schemes have been contemplated such as in the prior art to Schneeberger et al, U.S. Pat. No. 3,808,444 and the patent to Roder, U.S. Pat. No. 4,064,440. Such arrangements do not contemplate the use of digital read-outs with memory and storage of images of the object passing through the X-ray fan-beam.

An arrangement for detecting objects passing in an inspection viewing system utilizing a digital concept with memory has previously been provided in U.S. application Ser. No. 364,826, filed June 30, 1982, of which the present inventor is a co-inventor. Such an arrangement utilizes linear arrays of discrete detectors, such as photo diodes optically coupled to a phosphor, to assemble digitized images which are subsequently stored in a semiconductor main memory. Image resolution along the direction of the detector array is limited by the spacing between adjacent detectors, which spacing is typically about 1.5 mm.

The present invention is directed to a scheme for improving the image resolution to the size of the apertures in an oscillating mask to effectively at least double the resolving power of the array.

Such a scheme uses an oscillating mask in front of the linear array of detectors with a time-multiplexing of signals from the discrete detectors to multiply the pick-up. In this regard, each detector picks-up signals appearing at alternate sides of the detector face, which information is then stored in memory registers corresponding to alternate rows of final picture elements (or pixels). Sampling of the signals from the detectors is synchronized with the mask motion so that picture data are written into the appropriate memory registers. Thereafter, the signals are read-out from a main memory.

Figure 2A:
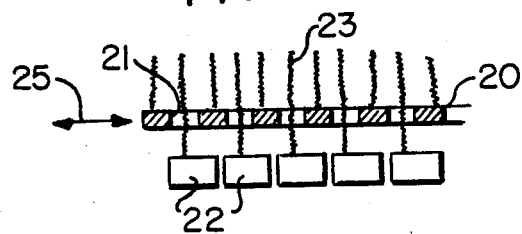
Figure 2B:
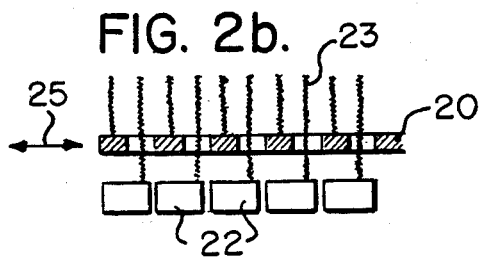
Figure 2C:
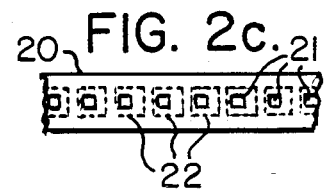
Figure 3:
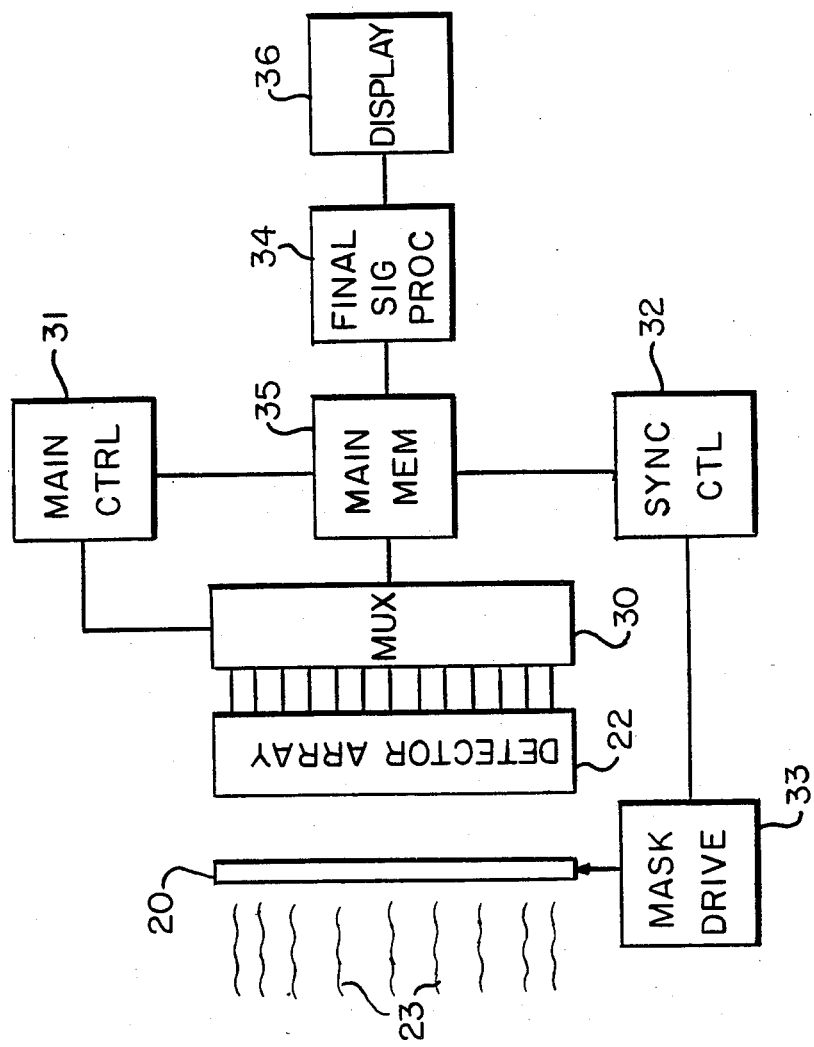

The features and arrangements of the present invention may be more clearly seen by reference to the drawing figures which illustrate without limitation aspects of the present invention, and wherein FIG. 1 illustrates the general arrangement of an inspection system utilizing the present invention, FIGS. 2a, 2b and 2c illustrate the arrangement and operation of the present invention, and FIG. 3 schematically illustrates a circuit arrangement of the present invention.

FIG. 1 illustrates the present invention utilized in a baggage detection system 1 wherein an X-ray fan-beam 2 is used. The fan-beam 2 is projected onto an item moving on a conveyer belt 4 which item is to be detected by the multi-element detector array 3. The multi-element detector array 3 involves at least one linear array of discrete detectors, such as photo-diodes which are optically coupled to a phosphor. Such an arrangement assembles digitized images which are thereafter stored in a memory.

The various components of the system may be accessed through a panel 8. Control of this system is provided at a control panel 6, and the items passing on the conveyer belt 4 may be viewed by way of the T.V. monitor 5. An X-ray generator is provided in the housing 7 to form the fan-beam 2 of X-rays onto the object or items passing on the conveyer.

The improvement according to the present invention involves the use of an oscillating masking arrangement in front of the detector elements. For example, as seen in FIGS. 2a, 2b and 2c, the oscillating mask 20 is provided adjacent to or in front of the detector array 22. The motion of the mask 20 is alternating, back and forth, in the directions 25.

The oscillating mask 20 has openings 21, which by oscillation, variously cause X-rays 23 to impinge at alternate portions or sides of the individual detector elements of the detector array 22. For example, as seen in FIG. 2a, the X-rays 23 impinge on the left sides of the detector elements, while in FIG. 2b the X-rays 23 impinge on the right sides of the detector elements. FIG. 2c show the arrangement of FIG. 2a looking through the oscillating mask 20 to the detector array 22.

The signals from the several discrete detector elements 22 are time-multiplexed in FIG. 3 by the multiplexer 30 under influence of main control 31 and operation of the mask synchronization control 32 to effectively double the resolving power of the array of detectors. For example, when the mask is in the "odd" position, such as illustrated in FIG. 2a, the data from the detectors 22 is stored in an "odd" row of memory registers in main memory 35, and selected by a signal from the sync. control 32. When the mask is in the "even" position as seen in FIG. 2b, data is stored in an "even" row of memory registers in main memory 35. The sampling of signals from the detector array 22, i.e. time-multiplexing, is appropriately synchronized with the mask motion by means of the mask drive 33 and mask sync control 32 so that the proper spatial relationship between points on the object is reproduced before storing pixel data in the main memory 35. The main memory 35 ultimately feeds a display 36 through signal processor 34.

Typical detector arrays contain about 500 discrete detector elements which are spaced by a distance of the order of 1.5 mm on the centers. These detector elements are scanned in a slow-scan rate of about 1/120 seconds. The scheme of the present invention effectively doubles the resolving power by driving the mask 20 with an amplitude of about 0.38 mm at a frequency of about 120 Hz. Peak acceleration for a sine-wave drive is therefore about 20 g's, and is an amount that is reasonable.

The ideal driving waveform for the oscillating mask 20 is a square wave, and the ideal driver could be a loud-speaker type coil and magnet arrangement.

As an alternative arrangement, signals from the detector array 22 may be fed into "odd" or "even" buffer memory registers for storage. These separate buffer memory registers then feed signals into the main memory 35.

Moreover, the concept of the present invention can be extended to triple or quadruple resolution. The practical limit is determined by the mask slit size and mask assembly acceleration requirements. For example, triple resolution could provide data alternately to the left sides, the central portions, and the right sides of the individual detector elements of the detector array 22.

While a single embodiment of the present invention has been illustrated and described, this arrangement does not limit the present invention. All structures, techniques, arrangements, and embodiments of the present invention which are evident from the claims are included in this invention.

What I claim:

1. In an object sensing device comprising a fan-beam of radiation, means for continually passing different objects through said fan-beam, a linear array of detector elements arranged to pick-up changes in intensity of said fan-beam caused by said objects, circuit means for sampling said detector elements, and electronic means for imaging said objects, the improvement comprising an oscillating mask between said objects and said detector elements, said mask being adjacent said detector elements, said mask having openings in registration with at most one-half of each of said detector elements, and said mask oscillating and moving within the area of each of said detector elements to expose alternate half portions of each of said detector elements.

2. A device according to claim 1, wherein said mask is oscillated at an amplitude of about 0.38 mm at a frequency of 120 Hz.

3. A device according to claim 1, wherein said means for passing objects is a conveyor structure.

4. A device according to claim 1, wherein said array of detector elements include about 500 discrete detector elements spaced by a distance of about 1.5 mm between centers of respective elements.

5. A device according to claim 1, wherein said radiation is X-radiation.

6. A device according to claim 1, wherein output signals from said alternate portions of said detector elements are stored in a main memory.

7. A device according to claim 4, wherein said output signals are time-multiplexed from said detector elements in synchronization with said mask motion.

8. A device according to claim 5, wherein resolving power of said electronic means is effectively doubled.

* * * * *